Figure 1:
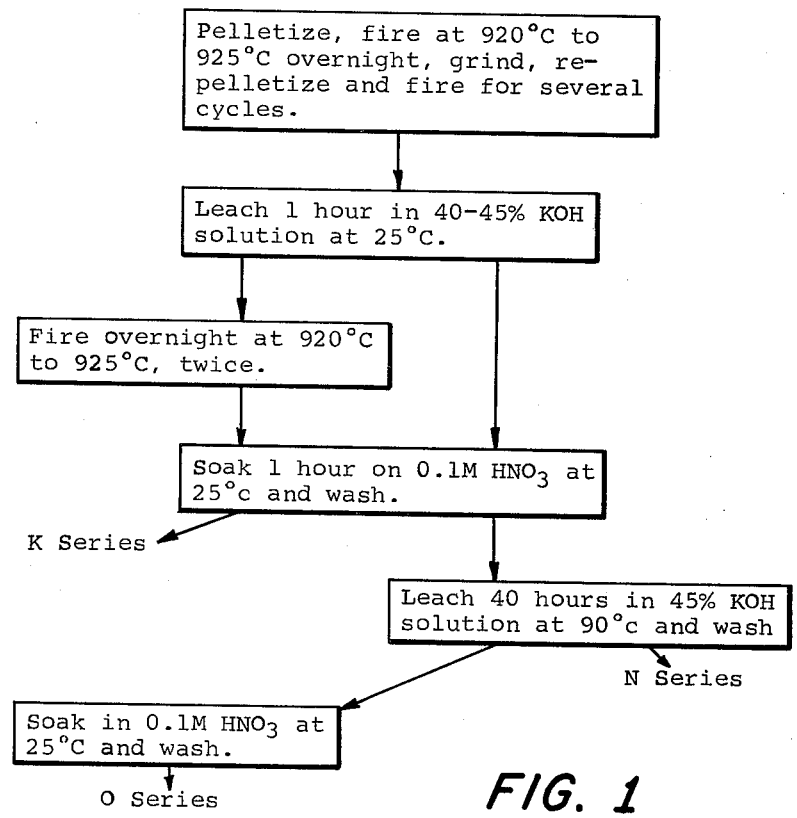

United States Patent [19]

Parry et al.

[11] 4,221,827
[45] Sep. 9, 1980

[54] METHOD OF MANUFACTURING A GAS SENSOR

[75] Inventors: John M. Parry, Sudbury, Mass.; Paul Raccah, Chicago, Ill.

[73] Assignee: The United States of America as represented by the Secretary of the Interior, Washington, D.C.

[21] Appl. No.: 970,878

[22] Filed: Dec. 19, 1978

[51] Int. Cl.$^2$ ............... G01N 27/04; H01C 13/00
[52] U.S. Cl. ............... 427/125; 73/23; 252/462; 338/34; 422/98; 423/263; 427/126.1
[58] Field of Search ............... 422/94–98; 338/34; 73/27 R, 23; 324/71 SN; 23/232 E; 252/462; 423/263; 427/125, 126

[56] References Cited

U.S. PATENT DOCUMENTS

| | | | |
|---|---|---|---|
| 3,897,367 | 7/1975 | Lauder | 252/462 |
| 3,922,204 | 11/1975 | Tseung et al. | 252/462 X |
| 3,951,603 | 4/1976 | Obayashi et al. | 73/27 R X |

FOREIGN PATENT DOCUMENTS

| | | | |
|---|---|---|---|
| 2533442 | 2/1976 | Fed. Rep. of Germany | 73/23 |
| 49-103699 | 1/1974 | Japan | 422/94 |
| 50-16695 | 2/1975 | Japan | 423/263 |

*Primary Examiner*—Arnold Turk
*Attorney, Agent, or Firm*—William S. Brown; Donald A. Gardiner

[57] ABSTRACT

A system for detecting carbon monoxide, even in the presence of methane, using a catalytic sensor material having a perovskite crystal structure and a composition $$A_{1-n} B_n CO_{3-m}$$

where A is a rare earth metal; B is an alkaline metal; C is a metal from the group consisting of cobalt, vanadium and maganese; O is oxygen; n is less than 0.1; and m is not greater than 0.5, which material is substantially free of oxides of A, B and C. The method of making the crystalline material involves firing appropriate amounts of mixed salts of A, B and C until substantially converted to the perovskite structure, and then leaching with a caustic to remove the undesired oxides.

11 Claims, 2 Drawing Figures

METHOD OF MANUFACTURING A GAS SENSOR

This inventions relates to the detection of gases and more particularly to apparatus for and method of detecting gases.

In recent years, much interest has been shown in gas sensors which detect a particular gas by a process whereby the molecular form of the gas is believed to be converted to ionic form, thereby providing an electronic charge transfer which can be detected. The latter then indicates the relative concentration of the gas. For example, in U.S. Pat. No. 3,732,519, there is disclosed a gas detecting device comprising a gas-permeable, metal oxide semiconductor body which exhibits a change in electron conductivity when contacted by a reducing gas in air. As the semiconductor materials, it is suggested that one can use oxides of tin, zinc, iron, titanium, nickel, cobalt or chromium. It is postulated that the metal oxide chemisorbs molecular oxygen onto the surface and catalyzes the gas to form oxygen ions, the catalysis reaching a fixed equilibrium at a given temperature. If carbon monoxide, for example, is present in the ambient atmosphere, the CO combines with the oxygen ions to form $CO_2$ although the metal oxide will continue to chemisorb $O_2$. This process provides a dynamic equilibrium in which the transfer of electrons to form ions changes the conductivity of the metal oxide. Such a structure is believed to respond to the presence of such gases as methane, carbon monoxide, alcohols and the like; the change in conductivity being proportional to the concentration of the oxidizable gas.

It is also known that lanthanum strontium cobaltite with a perovskite crystal structure, will catalyze oxygen in alkaline solutions, and is thus useful for polaragraphic oxygen electrodes as described in British Pat. No. 1352995 published May 15, 1974. However, there is reason to believe that lanthanum strontium cobaltite prepared according to this latter teaching is not useful to detect CO. Similarly, perovskite crystal structures formed of metal oxides containing cobalt and ruthenium or platinum have been shown to be quite useful as catalysts, and such uses are described in particular detail in U.S. Pat. No. 3,897,367.

The present invention comprises apparatus for and a method of detecting CO, particularly in the presence of $CH_4$, using a catalytic sensor material which is not necessarily stoichiometric and is believed to have a perovskite crystal structure broadly described by the structural formula $(A_{1-n}B_n)(C)(O_{3-m})$ where A is a rare earth metal ion, B is an alkaline earth metal ion, C is a metal ion selected from the group consisting of cabalt, vanadium, manganese and iron, O is oxygen, and n is less than 0.1 and m is not greater than 0.5, the sensor material being substantially free of unreacted oxides of the metals.

For example, in a preferred composition of the present invention A is lanthanum, B is strontium, C is cobalt, n is about 0.07 and m is about 0.

Other objects of the invention will in part be obvious and will in part appear hereinafter. The invention accordingly comprises the apparatus possessing the construction, combination of elements and arrangement of parts, and the process comprising the several steps and the relation of one or more of such steps with respect to each of the others, all of which are exemplified in the following detailed disclosure and the scope of the application all of which will be indicated in the claims.

Figure 2:
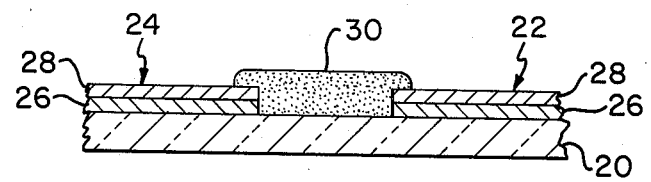

For a fuller understanding of the nature and objects of the present invention, reference should be had to the following detailed description taken in connection with the accompanying drawings wherein:

FIG. 1 is a flow diagram of methods of making the sensor of the present invention; and FIG. 2 is, in vertical section, a schematic diagram of a detector for detecting gas in accordance with the invention.

It is believed that the unique property of the present invention, i.e. ability to discriminate between CO and $CH_4$, arises out of the capability of the composition used in the present invention to catalyze the O—O bond at relatively low temperature.

For perovskites prepared by prior art methods, response (i.e. the changes in electrical characteristics) to carbon monoxide, if any, tends to deteriorate very quickly, typically within six days or less. This deterioration is now believed to be due to the presence of the free oxides, particularly of the rare earth metal or of the transition metals, which oxides had not been converted during firing. Such oxides in the presence of CO or $CO_2$ tend to convert to carbonates which are believed to impair the ability of the perovskite to catalyze the O—O bond.

Broadly, the present invention comprises a sensor formed of a mass of catalytic sensor material prepared according to the teachings of the present invention, and means for determining changes in the electrical characteristics of the mass occasioned by exposure thereof to the gas of interest, particularly carbon monoxide. In the usual form of the invention, the sensor material is coupled between a pair of electrical leads, all mounted on an electrically insulating substrate. It will be recognized by those skilled in the art that sensors of this type typically are intended to operate at elevated temperatures, e.g. 150° C.-200° C., and to that end the substrate may be in the form of a ceramic tube (which term is intended to include glass) the interior of which contains an electrical heating element, the sensor material and leads being mounted on the exterior of the tube. The general form of such sensors are well known and need not be further described here.

Specifically, the gas-sensitive material of the present invention is manufactured as a perovskite from thermally decomposable salts, such as oxalates or nitrates of the metals, in a mixture with appropriately selected proportions. The salts are converted onto a perovskite crystal structure of the type described, [i.e. $(A_{1-n}B_n)(C)(O_{3-m})$] which mixture is substantially free of individual oxides of the metals.

The manner in which the conversion can be effected for purposes of the invention is shown in the flow diagram of FIG. 1 in which the first step is to pelletize an appropriately proportioned mixture of the salts and fire the pellets in a oxygen-containing atmosphere such as air, at about 920° C. to 925° C. for several hours, typically overnight. While a single firing of this type converts a substantial proportion of the pellets to the desired perovskite, in order to obtain maximum conversion it is desirable to grind the pellets following firing, to repelletize the ground material and to refire the new pellets at about the same temperature for a similar period of time. This process should be repeated several times, typically five or six, in order to maximize the total conversion of the salts to the desired perovskite.

Perovskites prepared according to the first step of the present invention tend to contain a small but undesirable proportion of unreacted oxides of one or more of the metals. Consequently, following one or more firings of the pellets, as shown in FIG. 1, the pellets are leached in a caustic solution for a time sufficient to remove substantially all of the unreacted oxides. Typically, this leaching step involves maintaining the pellets in a 40%-45% KOH solution for one hour at room temperature, e.g. about 25° C. It is believed that this leaching step not only dissolves out unreacted oxides, but in addition selectively removes some of the ions of the heavy metal (cobalt, vanadium, manganese or iron as the case may be). Thus, for example where the perovskite is lanthanum strontium cobaltite, the removal of cobalt ions from the perovskite surface by the leaching step is believed to cause some tervalent cobalt ions to become $Co^{+4}$ in order to maintain charge neutrality in the lattice. The local effect of this is apparently to increase the surface population of tervalent ions, $Co^{+3}$, in the high spin state, and it is believed that these latter ions are largely responsible for the gas selectivity exhibited by the sensors of the present invention. At the same time, surface conductivity is desirably enhanced so that it becomes easier to measure changes in the electrical parameters of the material.

Following leaching, there are two alternative methods of preparing the gas sensing material. In one, the leached pellets are then reground, repelletized and refired for several hours at about 920° C.–925° C. once or twice, and the caustic is neutralized, typically by soaking the material preferably in ground form, in 0.1 M $HNO_3$ at room temperature and then washing out all solubles with a water rinse. The method as thus far described was used to form the gas-sensitive material for a series of sensors designated the K series.

In an alternative method, as shown in FIG. 1, following the caustic leaching step, the perovskite, instead of being fired, is soaked in the acid bath to neutralize the caustic and then washed. It is again then leached in caustic for a protracted period and at an elevated temperature, for example for 40 hours in 45% KOH solution at 90° C. The resulting perovskite material, when washed in water to remove residual KOH, was used to form a series, designated N, of the sensors of the present invention.

Another series of sensors, designated O, were prepared in the same manner as the N series, but subjected to an additional step in which the caustic was neutralized, as by treatment with 1.0 M $HNO_3$ at about room temperature, and a subsequent water wash.

From the perovskite material prepared as described and preferably in powder form, the sensors of the present invention as shown schematically in FIG. 2, were formed. On a ceramic substrate 20, typically a glass having a very high electrical resistance, a pair of spaced-apart electrical contacts 22 and 24 were disposed. Typically, each contact was first formed by depositing, by known techniques, layers 26 of chromium onto substrate 20, each layer 26 then being overcoated with a corresponding layer 28 of gold. A slurry of the preferred perovskite powder dispersed in a supporting medium, such as water with desirably a binder such as a 30% by weight polytetrafluorethylene dispersion, is spread as continuous mass 30 onto an open portion of the surface of substrate 20 betweeen and in physical contact with contacts 22 and 24. After drying the paste, the entire structure is preferably sintered, for example by heating at 300° C. for ten minutes.

The operation of sensors formed as thus described is described in the following examples:

EXAMPLE I

A sensor of the type shown in FIG. 2 was formed in which however contacts 22 and 24 were prepared by applying silver epoxy to substrate 20, platinum leads being embedded in the epoxy and the substrate being fired to cure the epoxy. The perovskite prepared was formed using $La_{0.9}Sr_{0.1}CoO_3$ as the gas-sensitive material. The resulting sensor was heated to 175° C. and in response to the introduction of 29 ppm CO, the resistivity changed from 18.1 KΩ to 21.4 KΩ. When similarly exposed to air containing 0.5% methane, the response was barely perceptable being about 0.5 KΩ. This response was confirmed in the presence of CO with a reproducibility of ±0.1 KΩ. At 200° C., better response and recovery times were noted, but some loss in sensitivity, the initial change of 3.3 KΩ at 175° C. being reduced to 1.8 KΩ at 200° C. Also the selectivity ratio in response to 30 ppm $CO$:0.05% $CH_4$ fell from 66:1 at 175° C. to 13:1 at 200° C.

EXAMPLE II

The K series of sensors prepared as earlier noted were tested primarily to observe whether or not deterioration of response, typical of prior art perovskites, had been overcome by using the perovskite prepared according to the present invention. Sensors thus prepared, although exhibiting fluctuations in time in the magnitude of response, still showed acceptable responses after nearly two months of testing.

EXAMPLE III

Similarly, the N series of sensors described above, all showed a very high if somewhat erratic response. Two such sensors showed some fading of response after six weeks of testing and storage at 200° C. In one case, continuous exposure to 47 ppm of CO in air for eight hours apparently caused some degradation, but two weeks later, the same sensor provided one of the best responses recorded to CO.

EXAMPLE IV

The O series sensors when tested in atmosphere of 47 ppm CO showed very high responses which were maintained over several weeks.

The foregoing examples are believed to confirm that using the techniques of the present invention, there is provided a carbon monoxide sensor in which there is substantially little or no degradation in response due to irreversible carbonate formation on the surface by reaction of either carbon monoxide or carbon dioxide with free metal oxides, thereby providing a comparatively long-lived carbon monoxide sensor which is highly selective in the presence of $CH_4$.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. A method of manufacturing a gas sensor comprising the steps of:

heating a mixture of salts of A, B, and C at a temperature and for at least one period of time sufficient to convert most of said mixture into a material having a perovskite crystal structure of the type:

$$A_{1-n}B_nCO_{3-m}$$

where
A is a rare earth metal;
B is an alkaline earth metal;
C is a metal selected from the group consisting of cobalt, vanadium, and manganese;
O is oxygen;
n is less than 0.1; and
m is not greater than 0.5; leaching substantially all oxides of said metals from said material; and
coupling a mass of said material between a pair of electrical leads.

2. The method of claim 1 wherein said step of coupling comprises
coating an electrically insulating substrate at two separate points with electrically conductive metal;
forming a paste from said material in a binder and applying said paste to form a bridge between said points; and
heating said bridge to form a dry mass of said material connecting said points.

3. The method of claim 2 wherein said step of coating comprises
forming a first coat of chromium at said points; and overcoating said chromium coat with gold.

4. The method of claim 2 wherein said paste is formed of a mixture of a powder of said material with polytetrafluorethylene.

5. The method of claim 1 wherein said heating and leaching steps comprise:
forming at least one pellet of a mixture of said salts;
firing said pellets at a temperature and for a period of time sufficient to effect at least partial conversion of said mixture to said perovskite structure;
at least one time grinding the fired pellets, forming new pellets from the ground pellets and refiring said new pellets at said temperature and for said period until most of said mixture is converted to said perovskite structure;
leaching the converted mixture with a caustic bath to remove substantially all oxides of said metals from said mixture; and
treating the leached mixture to neutralize said caustic.

6. The method of claim 5 wherein said temperature is about 920° C.–925° C.

7. The method of claim 5 wherein said caustic bath is a KOH solution.

8. The method of claim 5 wherein said leached mixture is treated with $HNO_3$.

9. The method of claim 5 wherein the step of at least one time grinding, firing and refiring is performed in part prior to the step of leaching and in part thereafter prior to the step of treating the leached mixture.

10. The method of claim 5 including after the step of treating a further step of leaching in caustic, and treatment of the mixture after said further step to neutralize the caustic added by said further step.

11. A method of manufacturing a carbon monoxide sensor comprising the steps of
heating a mixture of salts of lanthanum, strontium and cobalt to convert most of the mixture into a material having a perovskite crystal of the type $$La_{1-n}Sr_nCoO_{3-m}$$

where n is about 0.07 and m is approximately 0;
removing substantially all oxides of La, Sr and Co from said mixture; and
coupling a mass of the oxide-free mixture between a pair of electrical leads.

* * * * *